US00PP12073P2

(12) United States Plant Patent
Zary

(10) Patent No.: US PP12,073 P2
(45) Date of Patent: Aug. 28, 2001

(54) FLORIBUNDA ROSE PLANT NAMED 'JACZAP'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/400,727

(22) Filed: Sep. 21, 1999

(51) Int. Cl.[7] ..... A01H 5/00
(52) U.S. Cl. ..... Plt./141
(58) Field of Search ..... Plt./141, 130, 143, Plt./132

*Primary Examiner*—Howard J. Locker
(74) *Attorney, Agent, or Firm*—Klarquist Sparkman Campbell Leigh & Whinston, LLP

(57) ABSTRACT

A rose plant of the floribunda class having compact growth habit; large, bright orange, pink and yellow flowers having strong fragrance; glossy, dark green, healthy foliage; and good disease resistance.

1 Drawing Sheet

1

The present invention relates to a new and distinct variety of rose plant of the floribunda class which was originated by me by crossing the variety 'JACale', (U.S. Plant Pat. No. 5,860), with an unnamed seedling (not patented).

The primary objective of this breeding was to produce a new rose variety having the compact habit, bright blend of colors, large flowers and strong fragrance of the female parent, combined with the glossy, dark green, healthy foliage, vigorous growth and large flowers of the unnamed pink floribunda male parent. The objective was substantially achieved, along with other desirable improvements, as evidenced by the following unique combination of characteristics that are outstanding in the new variety and that distinguish it from its parents, as well as from all other varieties of which I am aware:

1. Bright orange, pink and yellow flowers;
2. Large flower size;
3. Strong fragrance;
4. Dark green, glossy foliage;
5. Vigorous, upright, well branched growth; and
6. Good disease resistance.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'JACale', (U.S. Plant Pat. No. 5,860).

*Pollen parent.*—Unnamed seedling (not patented).

Classification:

*Botanical.*—*Rosa hybrida.*

*Commercial.*—Floribunda.

2

FLOWER

Observations made from specimens grown in a garden environment at Somis, Calif. from March 1998 to August 1999.

Blooming habit: Continuous.

Bud:

*Size.*—About 1½ inches long when the petals start to unfurl.

*Form.*—The bud form is long, pointed ovoid.

*Color.*—When sepals first divide, bud color is Red Group 44C with some areas of Yellow-Red Group 23D where the sepal has just pulled away from the bud. When half blown, the upper sides of the outer petals are Red Group 37B on the outer ⅓ of the petal, fading to Red Group 37C. The inner ⅓ of the upper side is Yellow Group 12C that blends into Red Group 37C. The lower sides of the outer petals are Red Group 37C on the outer ⅔ of the petal. The inner ⅓ is Yellow Group 12C. When half blown, the upper and lower sides of the inner petals are Yellow-Orange Group 22B on the outer ⅔, while the inner ⅓ is Yellow Group 12C.

*Sepals.*—Color: Green Group 138B. Surface texture: Covered in fine hairs. There are three lightly appendaged sepals. There are two unappendaged sepals with hairy edges.

*Receptacle.*—Color: Yellow-Green Group 147B. Shape: Funnel. Size: Medium, about ⅜ inch×¼ inch. Surface: Smooth.

*Peduncle.*—Length: Short, averaging about 2 to 2½ inches. Surface: Glandular. Color: Yellow-Green Group 146C except when exposed to bright sunlight, then it is Greyed-Red Group 178B. Strength: Stiff, erect.

Bloom:

*Size.*—Large. Average open diameter is about 4½ inches.

*Borne.*—Singly, and several together in rounded clusters of three to five blooms.

*Stems.*—Strength: Strong. Average length is about 12–16 inches.

*Form.*—When first open: High centered. Permanence: Outer petals curl back.

*Petalage.*—Number of petals under normal conditions: 30.

*Color.*—The upper sides of the outer petals are Red Group 37B on the outer edge, fading to Red Group 37C toward the petal center. The inner ⅓ is Yellow Group 12C, blending into Red Group 37C. The upper sides of the inner petals are Yellow-Orange Group 22B on the outer ⅔, while the inner ⅓ is Yellow Group 12C. The reverse sides of the outer petals are Red Group 37C on the outer ⅔, while the inner ⅓ is Yellow Group 12C. The inner petals are Yellow-Orange Group 22B on the outer ⅔ while the inner ⅓ is Yellow Group 12C. The base of each petal has on both surfaces a small, ⅛ inch×⅛ inch, Yellow Group 13A half moon at the point of attachment. The major color on the upper sides is Red Group 37C.

*Variegations.*—None.

*Discoloration.*—The general tonality at the end of the first day: No change. At the end of the third day: No change. By day five, the upper surfaces of the petals have lost their yellow-orange color and have become Red Group 39A on the outer most petal edges, Red Group 37C on the middle petal edges, and Red Group 37C on the inner petal edges. The rest of the petal upper surface is Red Group 37C. By day seven, the upper surface has deepened to Red Group 42A. The lower surfaces have changed to Red Group 37C at day five to seven. By day eight, petal drop is beginning.

*Fragrance.*—Strong; tangerine.

Petals:

*Texture.*—Thick.

*Shape.*—Deltoid.

*Form.*—Tips slightly recurved.

*Arrangement.*—Imbricated. There are no petaloids in the center.

*Persistence.*—Petals drop off cleanly before drying.

*Lastingness.*—On the plant: Long (about seven to eight days). As a cut flower: Long (about eight to nine days).

Reproductive parts:

*Anthers.*—Size: Medium. Quantity: Many. Color: Yellow Group 12C. Arrangement: Regular around styles.

*Filaments.*—Color: Orange-Yellow Group 17C.

*Pollen.*—Present.

*Styles.*—Color: White Group 155B at the base, changing to Red Group 36C near the stigma.

*Stigmas.*—Color: Yellow-White Group 158B.

Plant:

*Form.*—Bush.

*Growth.*—Vigorous; upright; branching. At maturity, height is 36 to 42 inches, width is 24 to 30 inches.

Foliage: Number of leaflets on normal mid-stem leaves: Five.

*Size.*—Large (5½ to 6 inches long×4 to 4½ inches wide).

*Quantity.*—Abundant.

*Color.*—New foliage: Upper and lower surfaces: Greyed-Red Group 178A. Old foliage: Upper surface: Green Group 139A. Lower surface: Green Group 139B.

Leaflets:

*Shape.*—Broadly oval.

*Texture.*—Leathery; glossy.

*Edge.*—Serrated.

*Serration.*'Single; small.

*Petiole rachis.*—Color: Lower: Yellow-Green Group 147B; Upper: Green Group 139A.

*Petiole underside.*—Smooth, with occasional prickles.

*Stipules.*—Medium (about ½–¾ inch long), serrated; bearded.

*Disease resistance.*—Resistant to mildew and rust, susceptible to blackspot under normal growing conditions.

Wood:

*New wood.*—Color: Greyed-Red Group 178A. Bark: Smooth.

*Old wood.*—Color: Green Group 137A. Often, older wood has a Greyed-Red Group 178A cast to it if exposed to bright sun. Bark: Smooth Prickles:

*Quantity.*—On main canes from base: Many. On laterals from main canes: Many.

*Form.*—Medium; hooked slightly downward.

*Color when young.*—Greyed-Purple Group 183A.

*Color when mature.*—Greyed-Orange Group 166A.

Small prickles:

*Quantity.*—On main stalks: Few. On laterals: Few.

*Color.*—Greyed-Purple Group 183A when young, Greyed-Orange Group 166A when mature.

I claim:

1. A new and distinct variety of rose plant of the floribunda class, substantially as herein shown and described, characterized particularly by its compact growth habit; large, bright orange, pink and yellow flowers having strong fragrance; glossy, dark green, healthy foliage; and good disease resistance.

* * * * *

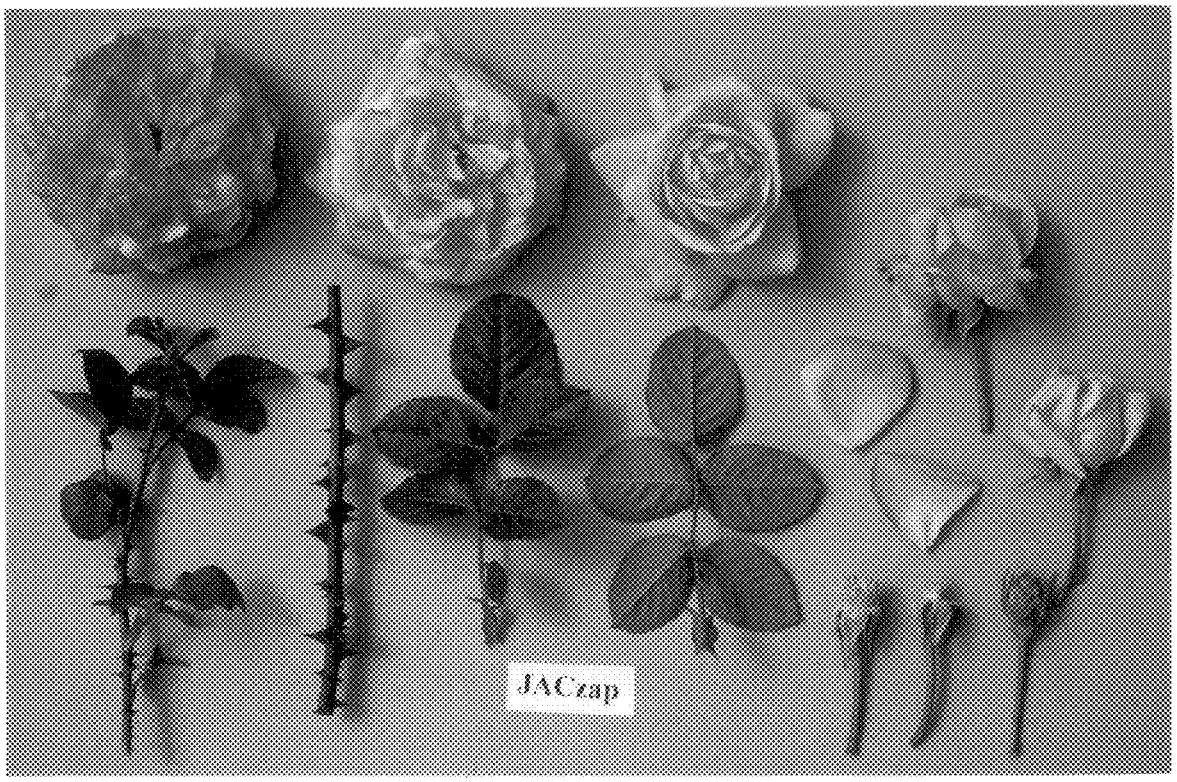
JACzap